United States Patent [19]

Hoffmann et al.

[11] 4,346,230
[45] Aug. 24, 1982

[54] PROCESS FOR THE PREPARATION OF DIMETHYL TEREPHTHALATE

[75] Inventors: Gerhart Hoffmann; Rudolph Cordes, both of Niederkassel-Ranzel; Wolfgang Merkel, Niederkassel, all of Fed. Rep. of Germany

[73] Assignee: Dynamit Nobel Aktiengesellschaft, Troisdorf, Fed. Rep. of Germany

[21] Appl. No.: 188,457

[22] Filed: Sep. 18, 1980

Related U.S. Application Data

[63] Continuation of Ser. No. 955,538, Oct. 30, 1978, abandoned, which is a continuation of Ser. No. 790,825, Apr. 25, 1977, abandoned, which is a continuation of Ser. No. 614,971, Sep. 19, 1975, abandoned, which is a continuation of Ser. No. 316,025, Dec. 18, 1972, abandoned.

[30] Foreign Application Priority Data

Dec. 18, 1971 [DE] Fed. Rep. of Germany ....... 2163031

[51] Int. Cl.³ .............................................. C07C 67/08
[52] U.S. Cl. .................................. 560/99; 252/431 C; 252/463; 252/471; 560/77; 562/412; 562/414
[58] Field of Search .................... 560/77, 99; 562/412, 562/414

[56] References Cited

U.S. PATENT DOCUMENTS

| | | | |
|---|---|---|---|
| 2,245,528 | 6/1941 | Loder | 560/77 |
| 2,894,978 | 7/1959 | Katzchmann | 560/77 |
| 3,253,017 | 5/1966 | Katzchmann | 560/77 |
| 3,845,100 | 10/1974 | Kusak | 560/77 |

FOREIGN PATENT DOCUMENTS

| | | |
|---|---|---|
| 747952 | 12/1966 | Canada . |
| 1114472 | 10/1961 | Fed. Rep. of Germany . |
| 2010137 | 9/1971 | Fed. Rep. of Germany . |
| 2144920 | 4/1972 | Fed. Rep. of Germany . |
| 43-9739 | 4/1968 | Japan . |
| 815198 | 6/1959 | United Kingdom . |

*Primary Examiner*—Natalie Trousof
*Assistant Examiner*—Vera C. Clarke
*Attorney, Agent, or Firm*—Craig and Antonelli

[57] ABSTRACT

A process for the preparation of dimethyl terephthalate by the oxidation of p-xylene/methyl p-toluate mixtures, preferably with air, esterification of the resulting acid products, and recycling of the methyl p-toluate to the oxidation stage, employs an oxidation catalyst consisting of a combination of cobalt and manganese compounds. The concentration of manganese ($Mn^{++}$) ranges between about 0.0001% and about 0.005% by weight.

9 Claims, No Drawings

PROCESS FOR THE PREPARATION OF DIMETHYL TEREPHTHALATE

CROSS-REFERENCE TO RELATED APPLICATION

This application is directed to an improvement of the invention disclosed in application Ser. No. 121,151 filed on Mar. 4, 1971 and is a continuation of application Ser. No. 955,538 filed Oct. 30, 1978, now abandoned, which application is a continuation of application Ser. No. 790,825 filed Apr. 25, 1977, which application is now abandoned and which is a continuation of application Ser. No. 614,971 filed Sept. 19, 1975, now abandoned, which in turn is a continuation of application Ser. No. 316,025 filed Dec. 18, 1972, now abandoned.

This invention relates to an improved process for the preparation of dimethyl terephthalate, and especially to a process using a catalyst system of higher selectivity, consisting of mixtures of cobalt and manganese, for the air oxidation of p-xylene/methyl p-toluate mixtures, in accordance with the general process of, for example, the German Patent Nos. 949,564 and 1,041,945, and the heretofore described application Ser. No. 121,151. The concentration of $Co^{++}$ and the concentration of $Mn^{++}$ in the reaction medium each ranges between about 0.005% and about 1% by weight in the process of the above noted application. These mixed cobalt-manganese catalysts, as compared to pure cobalt or pure manganese catalysts, result in a higher selectivity of the oxidation and thus in a higher yield of dimethyl terephthalate.

It has now been found that this increase in yield is also attained with substantially lower catalyst concentrations, especially with essentially lower manganese concentrations during the oxidation step. In particular, it has been found that the manganese concentration can be reduced to be in the range of from about 0.0001% to about 0.005%, and preferably from about 0.0005 to 0.001%. The advantage of a lower manganese concentration resides particularly in that, as compared to higher manganese concentrations, the same selectivity, but higher space-time yields can be obtained. It will be appreciated that the $Co^{++}$ concentration during the oxidation process is from about 0.005% to about 1% and preferably from about 0.005 to 0.05%.

Moreover, it has been discovered that the addition of manganese also exerts an advantageous effect on the esterification of the mixture of p-toluic acid/terephthalic acid monomethyl ester produced by the oxidation of the mixture of p-xylene/methyl p-toluate, due to a reduced formation of residue products. Accordingly, a further increase in yield is achieved, i.e. the yield increases from about 83 to 84% to about 85%. The advantageous effect of the addition of manganese on the esterification process is, however, not present at the very low manganese concentrations favorable for the oxidation step. It is, therefore, proposed in accordance with this invention to conduct the oxidation at first with low manganese concentrations and then add $Mn^{++}$ during the subsequent esterification of the oxidized product to obtain the concentration of $Mn^{++}$ up to about 1%.

While aqueous $Co^{++}$-and $Mn^{++}$-salt solutions such as for example the acetate salts can be employed during the oxidation, it is advantageous to utilize, for the esterification, an organic manganese salt soluble in organic solvents such as higher molecular weight fatty acids, naphthenic acids and aromatic carboxylic acid; for example, manganese ethylhexanoate. Exemplary of other suitable organic salts are the stearates and benzoates. Advantageously, the oxidation process can be conducted with still lower manganese concentrations than disclosed in application Ser. No. 121,151, and subsequently $Mn^{++}$ can furthermore be added for purposes of esterification. The quantities of cobalt and manganese ions, i.e. $Co^{++}$ and $Mn^{++}$, to be added during the oxidation reaction and during the esterification reaction are dependent on numerous conditions of process technology, such as, for example:

(1) concentration of the starting materials and final products; (2) number of stages; (3) reaction temperature; and (4) reaction pressure; both in the oxidation process or procedure and in the esterification step. Thus, the manganese concentration in the oxidation reaction can be increased from one stage to the next in accordance with the selected reaction conditions, and, after the oxidation, additional Mn catalyst can be introduced. The addition of manganese after the oxidation portion of the overall process can be omitted entirely, but such practice is less preferred.

The advantages of the process of this invention will be further understood from the following examples:

EXAMPLE 1

Into a reactor of stainless steel having a capacity of 1.5 cubic meters and equipped with an air feed pipe, a heating and cooling system, a vapor condenser, and a reaction water separator, 85 kilograms per hour of p-xylene and 130 kilograms per hour of methyl p-toluate are continuously introduced. The reactor charge is maintained at 1 cubic meter. As the catalyst, 0.72 liter per hour of a 3% aqueous Co-acetate solution is fed into the reaction vessel, so that a concentration of 100 p.p.m. of $Co^{++}$ is obtained in the aqueous reaction medium. Furthermore, 60 $Nm^3/h$. (where "$Nm^3$" equals volumetric quantity, cubic meters, at 0° C. and 1 atmosphere) of air is introduced. The temperature of the reactor is set to 160° C. and the pressure to 6 atmospheres gauge. The concentrations of $CO_2$ and CO in the waste gas, as well as the concentrations of formic and acetic acids in the reaction water are continuously analyzed. Evaluation of the analysis data shows the following amounts of by-products:

| | | |
|---|---|---|
| 2.15 kg./h. | - | $CO_2$ |
| 0.50 kg./h. | - | CO |
| 0.14 kg./h. | - | formic acid |
| 0.18 kg./h. | - | acetic acid |

The yield losses calculated on converted p-xylene are 7.6%.

EXAMPLE 2

Under the same conditions and using the same type of reactor set forth in Example 1, 0.65 liter per hour of a 3% aqueous Co-acetate solution and 0.07 liter per hour of a 3% aqueous Mn-acetate solution are fed to the reactor, so that a cobalt concentration of 90 p.p.m. and a manganese concentration of 10 p.p.m. are obtained in the aqueous reaction medium. The evaluation of the analysis data shows in this case the following quantities of by-products:

| | | |
|---|---|---|
| 1.35 kg./h. | - | $CO_2$ |

-continued

| | | |
|---|---|---|
| 0.37 kg./h. | - | CO |
| 0.11 kg./h. | - | formic acid |
| 0.16 kg./h. | - | acetic acid |

The yield losses calculated on converted p-xylene are 5%.

From this tabulation of data it will be seen that the process of this invention provides considerably less by-products during the oxidation reaction.

EXAMPLE 3

For the esterification of the acid mixture obtained according to Example 2, 800 kilograms of this oxidized product is filled into a stainless-steel reactor with a capacity of 1.5 cubic meters and equipped with a gas feed pipe, a heating and cooling system, a vapor condenser, and a receiver, at a temperature of 200° C. and under a pressure of 25 atmospheres gauge. Also, 100 kilograms per hour of methanol vapor are introduced into the reactor. When the acid number of the reaction mixture is about 5, the esterification reaction is terminated. The distillation of the reaction product results in 6.0% of residue corresponding a yield loss calculated on converted p-xylene of 8.3%.

EXAMPLE 4

An acid mixture obtained from Example 2 is reacted in methyl p-toluate under the same conditions as in Example 3, but with the addition of 100 p.p.m. $Mn^{++}$ in the form of 3% manganese ethylhexanoate solution in p-methyl toluate. The distillation of the reaction product yields an amount of residue of 4.8% corresponding to a yield loss calculated on converted p-xylene of 6.9%.

In order to demonstrate the optimum Mn concentration during the oxidation stage the following example is presented.

EXAMPLE 5

Under the same conditions and using the same type of reactor set forth in Example 1, different quantities of Co- and Mn-acetate solutions are fed to the reactor. The evaluation of the analysis data shows the following quantities of by-products:

| Number of Runs | Catalyst (ppm) | | Average acid number | By-products (kg/h) | | | |
|---|---|---|---|---|---|---|---|
| | Co | Mn | | $CH_3COOH$ | $HCOOH$ | $CO_2$ | CO |
| 8 | 150 | — | 126 | 0.15 | 0.12 | 2.1 | 0.5 |
| 4 | 149 | 1 | 125 | 0.11 | 0.11 | 1.6 | 0.4 |
| 2 | 140 | 10 | 124 | 0.14 | 0.11 | 1.4 | 0.3 |
| 2 | 120 | 30 | 117 | 0.15 | 0.14 | 1.3 | 0.3 |
| 2 | 100 | 50 | 120 | 0.13 | 0.15 | 1.4 | 0.4 |

While the novel principles of the invention have been described, it will be understood that various omissions, modifications and changes in these principles may be made by one skilled in the art without departing from the spirit and scope of the invention.

What is claimed is:

1. In a process for the preparation of dimethyl terephthalate by the air oxidation of a mixture of p-xylene and methyl p-toluate in a liquid reaction medium at a temperature of from about 80° to 250° C., by esterification of the resulting acid products with methanol, and by recycling of the methyl p-toluate to the oxidation stage, wherein a catalyst consisting of a mixture of cobalt and manganese compounds is employed during the oxidation stage and during the esterification stage, the improvement which comprises utilizing manganese during the oxidation stage in a concentration that is less than the concentration during the esterification stage, the manganese being in a concentration ranging between 0.0005% and 0.001% by weight during the oxidation stage and in a higher concentration resulting from the addition of about 0.001 to about 1% by weight of manganese during the esterification stage and utilizing cobalt in a concentration ranging from 0.005% to 1% by weight during the oxidation stage and the esterification stage, thereby increasing the yield of dimethyl terephthalate when compared with the use of higher manganese concentrations during the oxidation stage.

2. The process of claim 1, in which, during oxidation in a batchwise manner, the cobalt portion of the catalyst is added first and then the manganese portion is added.

3. The process of claim 1, in which, during oxidation and esterification in a multistage continuous manner, at least one of the cobalt or manganese portions of the catalyst is added partially in the first stage and partially in at least one of the subsequent stages of oxidation and esterification.

4. The process of claim 1, in which, additionally, in the subsequent esterification stage of the acid products about 0.001 to 0.1% by weight of manganese is added thereto.

5. The process of claim 1, in which the cobalt concentration in the reaction medium both oxidation and esterification stages is about 0.005 to 0.5% by weight.

6. The process of claim 1, in which the cobalt and manganese compounds are salts of cobalt and manganese which are soluble in the reaction medium or water-soluble salts.

7. The process of claim 1, in which the cobalt and manganese compounds are the cobalt and manganese salts of higher molecular weight fatty acids, naphthenic acids and aromatic carboxylic acids.

8. The process of claim 1, in which the cobalt and manganese compounds are oxides or hydroxides of cobalt and manganese.

9. The process of claim 1, in which the catalyst is a mixture of the ethyl hexanoic acid salts of cobalt and of manganese.

* * * * *